(12) United States Patent
Buriak et al.

(10) Patent No.: US 6,485,986 B1
(45) Date of Patent: Nov. 26, 2002

(54) FUNCTIONALIZED SILICON SURFACES

(75) Inventors: Jillian M. Buriak, West Lafayette, IN (US); Michael P. Stewart, Monroe, LA (US); Edward Robins, Great Shelford (GB)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/716,614

(22) Filed: Nov. 20, 2000

Related U.S. Application Data

(60) Provisional application No. 60/166,604, filed on Nov. 19, 1999.

(51) Int. Cl.[7] ............. G01N 33/552; C07K 17/14; C12Q 1/68; B05D 3/10
(52) U.S. Cl. ............. 436/527; 205/420; 435/6; 436/823; 525/106; 528/10; 530/391.1; 530/402
(58) Field of Search ............. 435/6; 205/420; 530/391.1, 402; 436/527, 823; 525/106; 528/10

(56) References Cited

U.S. PATENT DOCUMENTS 6,147,159 A * 11/2000 Hu et al.

FOREIGN PATENT DOCUMENTS

| WO | 9937409 A1 | * | 7/1999 |
| WO | 26019 A1 | * | 1/2000 |

* cited by examiner

Primary Examiner—Mary E. Ceperley
(74) Attorney, Agent, or Firm—Barnes & Thornburg

(57) ABSTRACT

The present invention is directed to a silicon substrate having a monolayer formed by an electrochemically-induced reaction between silicon hydride moieties on the silicon surface and optionally substituted alkynes covalently bound to the surface of the silicon substrate and to a method for electrochemically producing such a functionalized silicon substrate. The method of forming a covalently bound monolayer on a silicon surface comprises the steps of contacting the silicon surface with a $C_2$–$C_{24}$ alkyne and electrografting optionally substituted alkynes to the silicon surface.

9 Claims, 18 Drawing Sheets

FUNCTIONALIZED SILICON SURFACES

CROSS REFERENCE TO RELATED APPLICATIONS

This application claims priority under 35 U.S.C. §119(e) to U.S. Provisional Application Ser. No. 60/166,604, filed Nov. 19, 1999, which is expressly incorporated herein by reference.

FIELD OF THE INVENTION

This invention relates to surface functionalized silicon substrates. More particularly, this invention is directed to silicon surfaces having covalently bound monolayers formed by an electrochemically-induced reaction between silicon hydride moieties on the silicon surface and optionally substituted alkynes.

BACKGROUND AND SUMMARY OF THE INVENTION

Silicon surface chemistry is of fundamental technical significance because of the ubiquitous role of silicon in modem technology; yet silicon/organic chemistry is only just beginning to be investigated. Virtually all microprocessor chips in electronic products are based upon crystalline silicon wafers. Control of silicon surface chemistry is crucial to allow access to technologically functional thin films for fabrication of new electronic devices. In 1990, Canham and co-workers showed that silicon wafers could be etched using hydrofluoric acid to produce a porous layer that is only a few microns thick (termed porous silicon) and exhibits photoluminescence upon exposure to UV light (Canham, L. T. AppL. Phys. Lett. 1990, 57, 1046). The surface of porous silicon (Si) is populated with metastable Si—$H_x$ bonds (x=1,2,3), exposed Si—Si bonds, and defects such as open valence, "dangling" Si atoms. Potential applications for porous silicon include uses as chemical sensors, biosensors, optoelectronic devices such as electroluminescent displays, photodetectors, mass spectrometry (desorption ionization on silicon or DIOS), interfacing with neurons and other nerve cells, and as a matrix for photopumped tunable lasers. As a result, modification and characterization of photoluminescent porous silicon surfaces has become an area of intense interest.

Recent developments in the functionalization of porous silicon have enabled Si—C bonds to be formed on the porous—Si surface by attacking the weak Si—Si bonds of exposed nanocrystalline submaterial with Grignard or alkyllithium reagents. Grignard and alkyllithium transmetallation and the use of Lewis acid catalysis have also been used to exploit the great population of surface Si—H bonds. Thermal, radical-mediated, and UV photolytic alkene hydrosilylation has also been reported for flat Si and Si hydride surfaces. In general, chemistry that works on porous silicon also applies to flat Si (100) and Si (111) surfaces based on substantial literature precedent. Additionally, using the Si surface as a semiconducting electrode, several workers have recently reported electrochemical Si—C bond formation by direct grafting, an approach with few parallels to soluble, molecular silane chemistry.

The present invention is directed to a new method of functionalizing the Si surfaces by electrochemically grafting terminal alkynes to silicon resulting in two distinct surface derivations depending on the polarity of the surface bias. Cathodic electrografting (CEG) directly attaches alkynes to the surface, whereas anodic electrografting (AEG) of alkynes yields an alkyl surface.

DETAILED DESCRIPTION OF THE INVENTION

Figure 1:
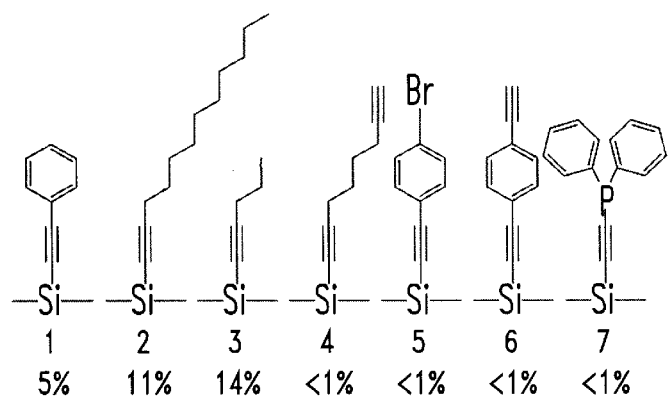
FIG. 1. Representative surfaces prepared by CEG of alkynes to porous silicon. The boldface numbers refer to 1) phenylacetylene, 2) 1-dodecyne, 3) 1-pentyne, 4) 1,7-octadiyne, 5)p-Br-phenylacetylene, 6) 1,4-diethynylbenzene, and 7) diphenylphosphinoacetylene. The percentage below each surface represents the % photoluminescence remaining after functionalization by CEG.

The term "$C_1$–$C_x$–alkyl" refers to a straight, branched or cyclic alkyl group having the designated (x) number of carbon atoms. It is understood that, if the group is cyclic, it must have a minimum of three carbon atoms.

The term "primary, secondary or tertiary amino" represents an $R^5R^6N$-group wherein $R^5$ and $R^6$, independently, represent a hydrogen, $C_1$–$C_6$ alkyl or an aryl.

The term "optionally substituted phosphino" refers to a group of the formula $R^5R^6P$- wherein $R^5$ and $R^6$ are as defined below.

The term "optionally substituted borane (1) and borane (2)" refers to a borane (1) or borane (2) group having one or more substituents independently selected from the group consisting of hydrogen, hydroxy, $C_1$–$C_{12}$ alkoxy, $C_1$–$C_6$ alkyl, thiol and aryl.

The terms "aryl" and "heteroaryl" are used as they are understood in the art. Examples of useful aryl groups are benzyl and naphthyl. Heteroaryl groups having one or more hetero-ring atoms, wherein at least one heteroatom is nitrogen are particularly useful in the methods and compositions of this invention. Examples of such groups include pyridyl, pyrrolyl, bipyridyl phenanthrolyl, pyrazinyl and indolyl.

The term "DNA or RNA analog" refers to a chemical analog of DNA or RNA having other than a phosphate linked sugar "backbone" that is capable of forming a double stranded complex with DNA or RNA.

This invention provides a general method for covalent modification of the surface of silicon through attachment of readily available alkynes mediated by cathodic or anodic electrografting. Alkynes subjected to anodic electrografting or cathodic electrografting in the presence of surface bound Si—H groups react with the Si—H groups to yield surface bound alkyl or alkyne groups, respectively, as outlined in scheme 1.

Scheme 1. AEG and CEG of alkynes to a porous silicon surface.

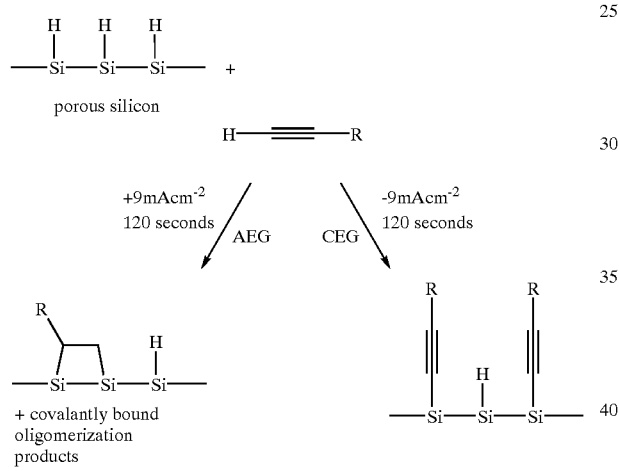

Alkynes subjected to cathodic electrografting in the presence of surface bound Si—H groups react with the Si—H groups to yield surface bound alkyne groups according to a mechanism that was determined based on data such as acid quenching and infrared spectra data (see examples) and is outlined in scheme 2.

Scheme 2. CEG-promoted hydrosilylation of alkyne groups.

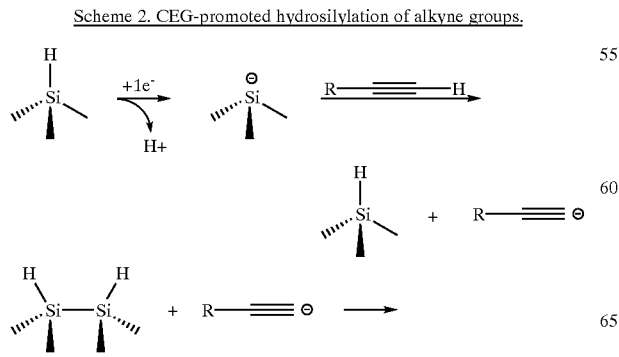

-continued

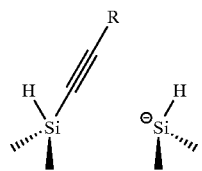

Figure 12:
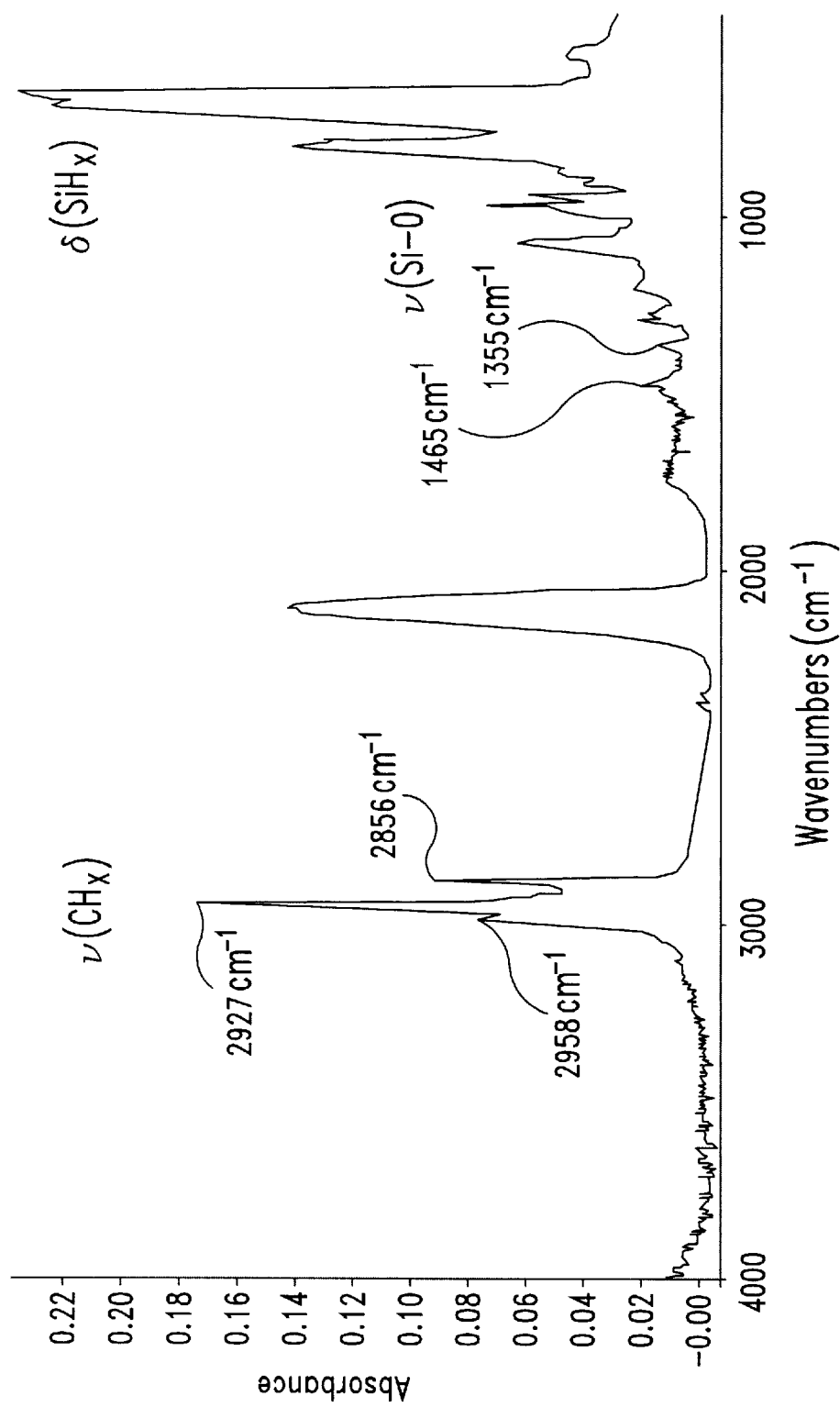
FIG. 12. CEG of 1-dodecanethiol.

The results of the CEG experiments suggest that the CEG reaction proceeds via a silyl anion intermediate formed by reduction of surface Si—H bonds in a space charge layer (see scheme 2) to yield either H or ½H$_2$. The silyl anion species has been previously inferred for the mechanism of alkylhalide grafting. The subsequent in situ generation of a carbanion from deprotonation of the weakly acidic alkyne leads directly to nucleophilic Si—Si bond attack, as previously observed. The silyl anion is quenched in the presence of a proton source (0.1 M HCl in diethyl ether), leading to no incorporation of alkyne. Other weakly acidic moieties can be grafted via this CEG reaction, such as 1-dodecanethiol (see FIG. 12), presumably through a similar deprotonation step and subsequent attack of Si—Si bonds by an RS$^-$ species. Minor incorporation of butyl groups (2956, 2923, and 2872 cm$^{-1}$), which may be due to tenacious physisorption or electrochemical decomposition of the Bu$_4$NPF$_6$ electrolyte, is observed in all CEG reactions. The butyl groups are not removed after 30 minutes in boiling chloroform.

Alkynes subjected to anodic electrografting in the presence of surface bound Si—H groups react with the Si—H groups to yield surface bound alkyl groups according to a mechanism that was determined based on infrared spectra data (see examples) and is outlined in scheme 3.

Scheme 3. AEG-promoted hydrosilylation of alkyne groups.

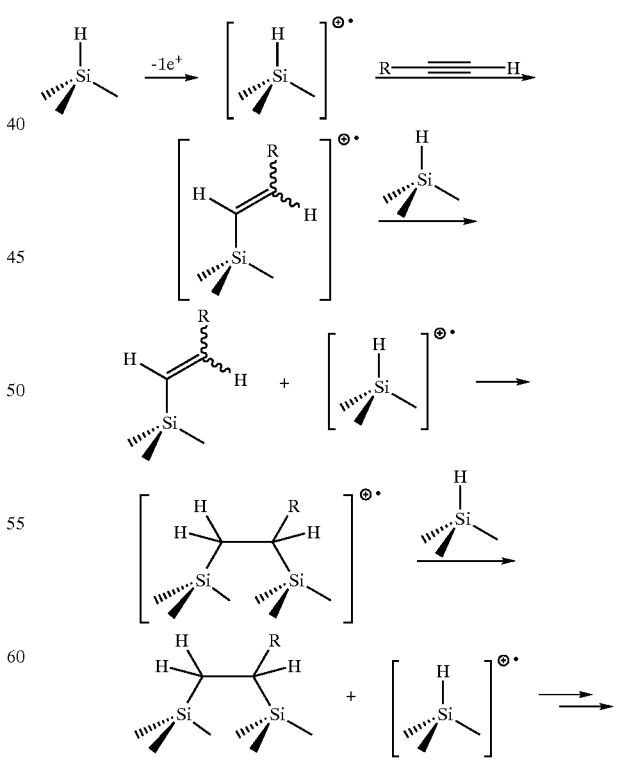

In accordance with one embodiment of the present invention a method for forming a covalently bound monolayer of organic substituents on a porous silicon substrate having a surface comprising silicon hydride groups is provided. The method comprises the steps of contacting the surface of the porous silicon substrate with an electrically conductive, substantially oxygen-free, aprotic organic solvent solution comprising an optionally substituted $C_2$–$C_{24}$ alkyne, positioning a conductor electrode in electrical current flow communication with the solution, and applying an electrical potential to the solution between the porous silicon surface and the conductor electrode sufficient to induce electrical current flow through the solution between the porous silicon surface and the conductor electrode for a period of time sufficient to covalently bind at least a portion of the alkyne to the porous silicon surface.

In accordance with another embodiment of the invention a method for forming a covalently bound monolayer of organic substituents on a flat Si (100) or Si (111) surface is provided. The method comprises the same steps as described in the preceding paragraph.

The electrically conductive aprotic organic solvent solution of the present invention includes any aprotic organic solvent capable of dissolving an amount of an organic salt sufficient to enable the solution to conduct current responsive to a potential capable of effecting anodic or cathodic electrografting of alkynes onto silicon surfaces. These aprotic organic solvents may include solvents such as dioxane, dimethylformamide, dimethylacetamide, sulfolane, N-methyl pyrrolidine, dimethylsulfone, dichloroethane, trichloroethane, and freons, or solvents such as dichloromethane, acetonitrile, and tetrahydrofuran. The organic salt, which when dissolved in the solvent, enables the solvent solution to conduct a current in response to application of a potential is preferably a tertiary amine salt of a strong acid or a quaternary ammonium salt having an associated anion corresponding to a strong acid. Exemplary of such anions are tetrafluoroborate, perchlorate, perfluorosulfate, hexafluorophosphate, trifluoroacetate, and like anions. Organic salts comprising other quaternary ammonium salts and other solvent-soluble organic salts are also applicable to the invention. The organic salt solutions used in the present process are preferably substantially anhydrous and substantially oxygen-free. The solutions are preferably maintained under dry oxygen-free conditions such as that provided by an inert atmosphere, e.g., nitrogen, or a noble gas.

In carrying out the method of the present invention, an electrical current is generated in a solvent solution in contact with the silicon surface. The organic solution comprises an amount of an alkyne, as described more specifically herein below, effective to form a substantially uniform organic monolayer on the surface of the silicon substrate during electrochemical deposition. A conductor electrode is positioned in electrical current flow communication with the organic solvent solution, and an electrical potential is applied to the solution between the silicon surface and the conductor electrode. The potential should be sufficient to induce electrical current flow through the solution between the silicon surface and the conductor electrode for a period of time sufficient to covalently bind at least a portion of the alkyne to the silicon surface. The conductor electrode can include any conductive material such as a platinum, paladium, silver, gold, or graphite electrode. The duration of the applied potential should be sufficient to covalently bind at least a portion of the alkyne to the silicon surface. In one embodiment of the invention, the potential is applied for a period of time during which current flow relative to current flow at the original potential falls to a value less than 50% of the original current, that time being sufficient to form a continuous monolayer (of alkyne or alkyne derivative) on the silicon surface. In a preferred embodiment of the invention, the threshold electrical potential applied induces a current flow of about 10 mA/cm$^2$ for electrografting and the potential is applied for about 120 seconds. The current density is not critical and the required duration of the applied potential is typically inversely proportional to current density.

Cathodic and anodic electrografting in accordance with the invention are carried out on the silicon substrate in an aprotic organic solvent solution that is substantially oxygen-free because oxidation of the substrate occurs under ambient conditions and surface oxidation appears to compete with covalent binding of alkynes to the silicon substrate. A preferred method of maintaining a substantially oxygen-free solvent solution is to carry out the electrochemical deposition in an inert atmosphere, e.g., in a glove box which has been evacuated of oxygen and filled with nitrogen. It is contemplated that other methods, normally occurring to one skilled in the art, of creating a substantially oxygen-free environment will be applicable to the invention.

In accordance with the method of the present invention the aprotic organic solvent solution comprises optionally substituted $C_2$–$C_{24}$ alkynes. These alkynes may include, for example, 1-pentyne, 1-dodecyne, 1,7-octadiyne, phenylacetylene, p-Br-phenylacetylene, 1,4,-diethynylbenzene, diphenylphosphino-acetylene, and 1-dodecanethiol, and any other alkyne capable of being electrografted onto a silicon substrate by anodic electrodeposition or cathodic electrodeposition, a providing alkyl substituted and alkynyl substituted surfaces, respectively.

This surface may be made homogenous, consisting of a single type of alkyne or alkyl group, where the silicon surface is electrografted with a single type of alkyne via CEG or AEG, respectively. Alternatively, the surface may be made heterogeneous, consisting of different types of alkyne groups where CEG is performed using two or more selected alkynes, or consisting of different types of alkyl groups where AEG is performed using two or more selected alkynes. In the case of a heterogenous surface monolayer, the mole fraction of the groups in the monolayer would correspond generally to the mole fractions of the different types of alkynes in the reagent mixture used to form the monolayer. The functional groups present on any of the alkyne reactants are preferably in a "protected" form during the electrodeposition step and are thereafter deprotected on the surface to provide reactive sites for further surface functionalization, i.e., for coupling to biologically significant molecules using standard ester- or amide-forming coupling techniques. The term "protected" refers to the use of standard protecting groups that can serve to prevent unwanted reaction of reactive functional groups during one reaction (i.e., electrodeposition) and thereafter be removed to regenerate the reactive functional groups for subsequent reactions. Such protecting groups are well-known in the art.

In another embodiment of the invention, patterns of covalently bound species derived from alkynes on the silicon surface can be formed by sequential photopatterning and electrografting procedures. In accordance with this embodiment, photopatterning of alkyl and alkynyl monolayers on porous silicon surfaces is controlled by art-recognized masking and demasking techniques. The patterned, unmasked, nonfunctionalized silicon hydride groups can be selectively reacted with a particular alkyne or a mixture of alkynes using CEG or AEG.

In one aspect of this method, the $C_2$–$C_{24}$ alkyne is a compound of the formula:

$$R^1—C≡C—R^2$$

wherein $R^1$ is hydrogen and $R^2$ is hydrogen, hydroxy, halo, cyano, isocyano, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, borane (1) or borane (2), or $C_1$–$C_{18}$ alkylthioether or an optionally substituted $C_1$–$C_{18}$ alkyl, aryl, heteroaryl or vinyl group; and when $R^2$ is a substituted group, the group is substituted with one or more substituents selected from the group consisting of hydroxy, halo, cyano, isocyano, $C_2$–$C_{24}$ alkynyl, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, aryl, borane (1) or borane (2), or $C_1$–$C_{18}$ alkylthioether, halo $C_1$–$C_{18}$ alkyl, cyano $C_1$–$C_{18}$ alkyl, isocyano-$C_1$–$C_{18}$ alkyl, $C_1$–$C_{18}$ carbamido, or $C_1$–$C_{18}$ alkylthio group, a $C_1$–$C_{18}$ ferrocene substituent or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA.

In another embodiment, any hydroxy, carboxy, amino or thiol substituent group is in the form of protected hydroxy, protected carboxy, protected amino and protected thiol, respectively.

This invention further provides a silicon substrate having a surface comprising a covalently bound monolayer wherein the monolayer comprises a group of the formula:

$$R—C≡C—Si$$

wherein

Si is a surface silicon atom through which the substituted or unsubstituted alkynyl group is bonded to the silicon surface; and R is hydrogen, hydroxy, halo, cyano, isocyano, $C_1$–$C_{18}$ alkoxy, $C_1C_{-18}$ carboxy, $C_1$–$C_{18}$ alkoxycarbonyl, primary, secondary or tertiary amino, thiol, optionally substituted phosphino, borane (1) or borane (2), or $C_1$–$C_{18}$ alkylthioether or an optionally substituted $C_1$–$C_{18}$ alkyl, aryl, heteroaryl or vinyl group; and when R is a substituted group, the group is substituted with one or more substituents selected from the group consisting of hydroxy, halo, cyano, isocyano, $C_2$–$C_{24}$ alkynyl, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, aryl, borane (1) or borane (2), or $C_1$–$C_{18}$ alkylthioether, halo $C_1$–$C_{18}$ alkyl, cyano $C_1$–$C_{18}$ alkyl, isocyano-$C_1$–$C_{18}$ alkyl, $C_1$–$C_{18}$ carbamido, or $C_1$–$C_{18}$ alkylthio group, a $C_1$–$C_{18}$ ferrocene substituent or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA; or R, together with the carbon atoms to which it is attached, forms a 5-, 6-, 7- or 8-membered ring.

The invention also provides for a silicon substrate having a silicon surface comprising a covalently bound monolayer, said monolayer comprising a group of the formula:

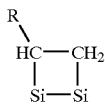

wherein

Si is a surface silicon atom; and

R is hydrogen, hydroxy, halo, cyano, isocyano, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, borane (1) or borane (2), or $C_1$–$C_{18}$ alkylthioether or an optionally substituted $C_1$–$C_{18}$ alkyl, aryl, heteroaryl or vinyl group; and when R is a substituted group, the group is substituted with one or more substituents selected from the group consisting of hydroxy, halo, cyano, isocyano, $C_2$–$C_{24}$ alkynyl, $C_1$–$C_{18}$ alkoxy, $C_1$–$C_{18}$ carboxy, $C_1$–$C_{18}$ alkoxycarbonyl, primary, secondary or tertiary amino, thiol, optionally substituted phosphino, aryl, borane (1) or borane (2), or $C_1$–$C_{18}$ alkylthioether, halo $C_1$–$C_{18}$ alkyl, cyano $C_1$–$C_{18}$ alkyl, isocyano-$C_1$–$C_{18}$ alkyl, $C_1$–$C_{18}$ carbamido, or $C_1$–$C_{18}$ alkylthio group, a $C_1$–$C_{18}$ ferrocene substituent or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA; or R together with the carbon atoms to which it is attached, forms a 5-, -, 6-, 7- or 8- membered ring.

Preferred aspects of this invention are those silicon surfaces that contain bound alkyne groups where $R^2$ is an aryl or heteroaryl or phosphino metal chelating ligand and any metal complex of this metal chelating ligand.

Another preferred aspect of this invention are those silicon surfaces wherein at least a portion of the covalently bound $R^2$ group comprises a biologically significant ligand.

Hydrosilylation of alkynes with surface situated silicon hydride groups on a silicon surface promoted by electrografting yields a wide variety of chemical groups covalently bound to the surface. The present method is tolerant of alkynes substituted with functional groups such as phenyl, alkyl, and phenylphosphino groups which can be used to form covalently bound monolayers on silicon surfaces without additional protecting groups.

Another advantage of this invention is that it allows formation of a surface-protecting monolayer under relatively mild conditions, i.e., at room temperature (about 20–25° C.) Moreover, silicon having a monolayer of covalently bound organic groups demonstrates remarkable chemical resistance. For example, when silicon functionalized with organic groups using this method was subjected to boiling in aqueous NaOH solution (pH 10), no oxidation was seen and only minor changes in the surface IR spectra were noted. When nonfunctionalized silicon is subjected to those same conditions, the layer is destroyed in approximately 180 seconds. Because of the high stability displayed by silicon surfaces protected in accordance with this invention, this methodology represents an important step towards the use of silicon in technologically important applications.

In order to illustrate the operation of this invention, the following non-limiting examples are provided:

EXAMPLE 1

Preparation of Porous Silicon and FT-IR and Photoluminescence Measurements

FT-IR spectra. The spectra were collected using either a Perkin-Elmer 2000 or a Nicolet Nexus 670 FT-IR spectrometer with a DTGS detector, in transmission mode, typically obtained at 4 cm$^{-1}$ resolution with 16 or 32 scans collected, respectively.

Preparation of porous silicon. Porous silicon (1.12 cm$^2$) was prepared by anodization of prime-grade n-type, P-doped, 0.65–0.95 Ω-cm silicon. The etching was carried out with a 24% HF/24% H$_2$O/52% ethanol etching solution for 3 minutes at +76 mA cm$^{-2}$ under 25 mW cm$^{-2}$ white light illumination. The applied current was controlled using an EG & G instruments, Princeton Applied Research Potentiostat/ Galvanostat Model 363 instrument in constant current mode. After anodization samples were washed with ethanol and hexane before being dried under a stream of nitrogen.

Photoluminescence measurements. PL measurements were recorded using an Oriel 250 W mercury arc lamp and a Bausch and Lomb monochromator set to 450 nm as the excitation source. Emission was observed through a 495 nm LWP filter (GG495) with an Acton Research Spectra Pro 275 monochromator (0.275 m) and Princeton Instruments liquid N$_2$ cooled CCD detector (model LN/CCD-1024-E/1).

Syntheses of 1-phenyl-2-(trimethylsilyl)acetylene and 1-trimethvlsilyldodecyne. Syntheses of 1-phenyl-2-(trimethylsilyl)acetylene and 1-trimethylsilyldodecyne were achieved using a method similar to that reported by C. Eaborn and D. R. M. Walton, *J. Organomet. Chem.*, 1965, 4,217, reaction conditions which are directly analogous to those reported by Weber in W. P. Weber, *Silicon Reagents for Organic Synthesis*, Springer-Verlag, New York, 1983, p. 150.

EXAMPLE 2

Preparation of Functionalized Silicon by Electrografting

Electrografting. Electrochemical grafting is carried out in a Vacuum Atomospheres Nexus One glove box filled with nitrogen. AEG and CEG carried out on porous silicon under ambient conditions results in large-scale oxidation of the surface with surface oxidation appearing to be in competition with the alkyne grafting. An ohmic contact is established between the backside of the porous Si sample and a sheet of aluminum foil. A 35–40 μl aliquot of alkyne and 1 ml of 0.1 M tetrabutylammonium hexafluorophosphate in CH$_2$Cl$_2$ are applied to the porous Si sample and a platinum loop is used as the counter electrode. A current is then applied (+10 mA for AEG, −10 mA for CEG), typically for 120 seconds. Afterwards, the sample is removed from the glove box, and gently washed with CH$_2$Cl$_2$/pentane and dried under a nitrogen stream. The porous Si surfaces are then characterized by transmission mode FT-IR spectroscopy.

EXAMPLE 3

FT-IR Analysis of CEG Phenylacetylene

Figure 4:
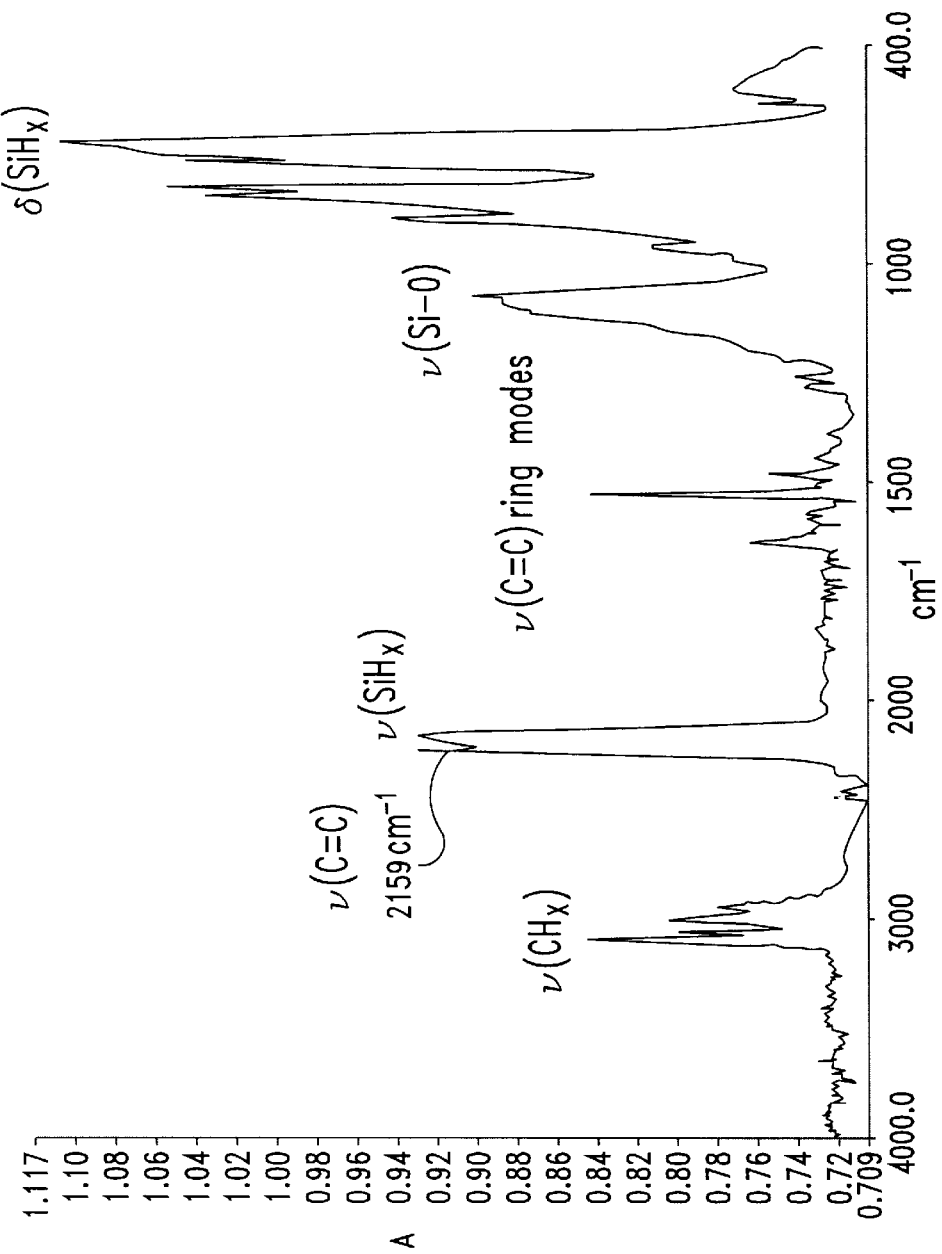
FIG. 4. CEG of phenylacetylene.

The same general procedures for preparation of porous silicon, electrografting, and FT-IR spectra measurements were followed as set forth in examples 1 and 2. FT-IR analysis of CEG phenylacetylene reveals Si—H$_x$ stretches which are broadened and decreased in integrated intensity compared to unmodified porous silicon. The absence of a ν(≡C—H) mode around 3300 cm$^{-1}$ and an observed sharp silylated alkyne ν(C≡C) at 2159 cm$^{-1}$ is consistent with a Si-alkynyl surface and not simple physisorption. For instance, the ν(C≡C) of 1-phenyl-2(trimethylsilyl)-acetylene appears at 2160 cm$^{-1}$ while that of phenylacetylene is observed at 2110 cm$^{-1}$ (see FIG. 4).

EXAMPLE 4

FT-IR Analysis of CEG 1-Dodecyne

Figure 2:
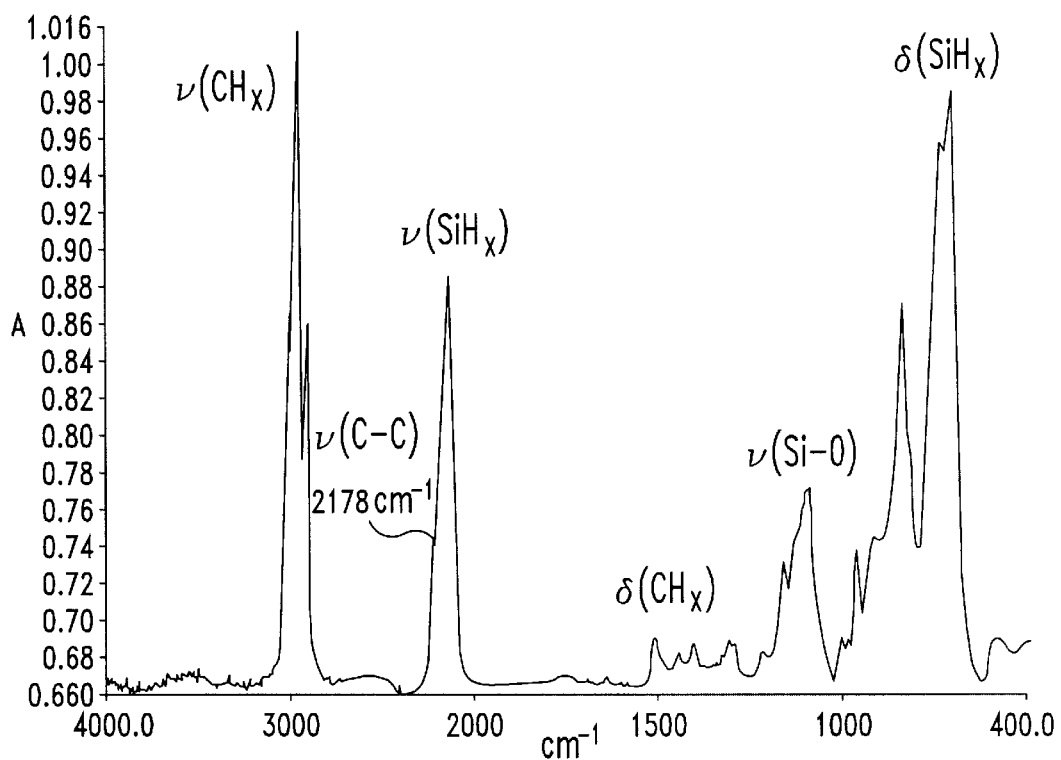
FIG. 2. CEG of 1-dodecyne.
Figure 3:
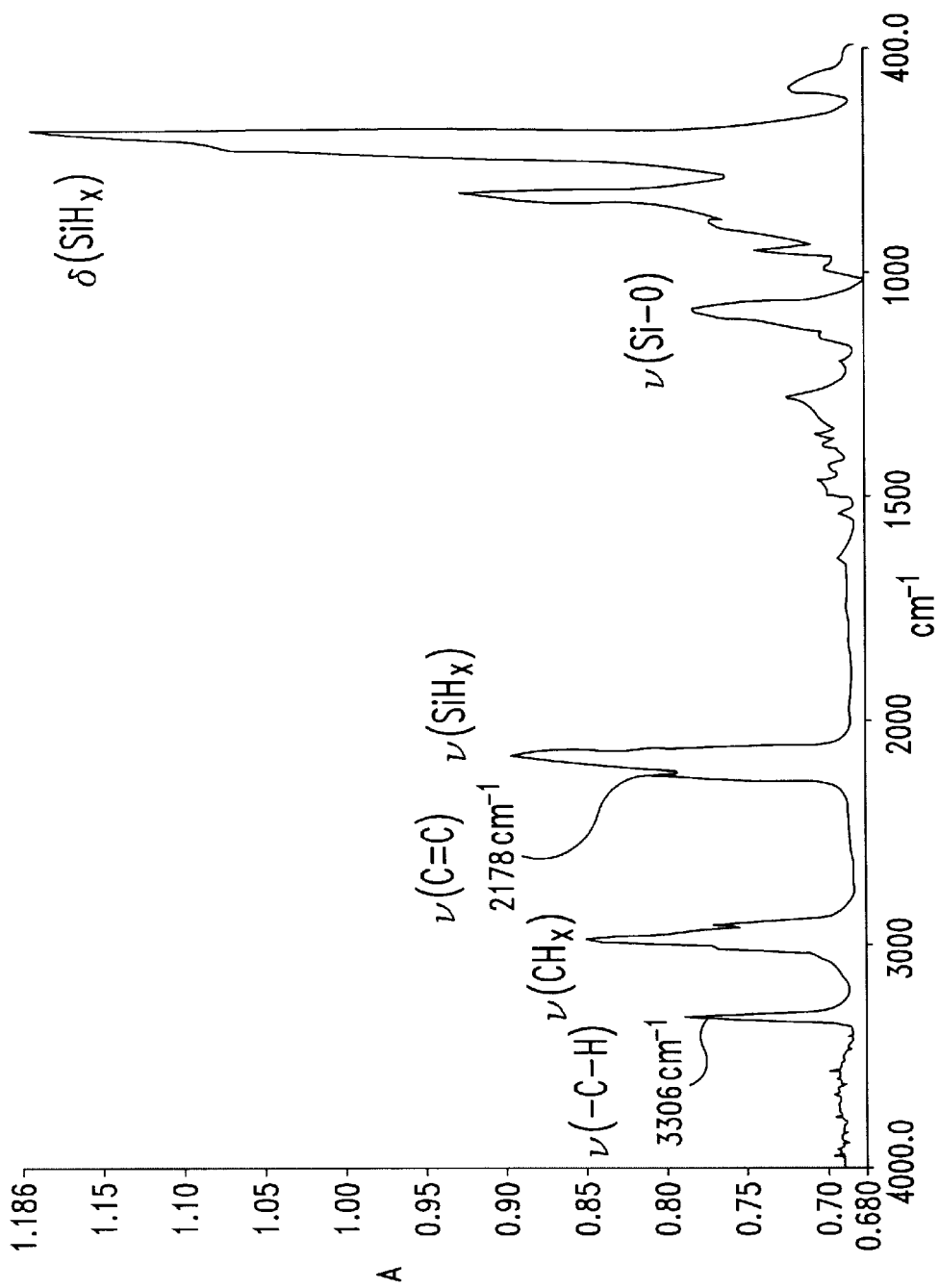
FIG. 3. CEG of 1,7-octadiyne.

The same general procedures for preparation of porous silicon, electrografting, and FT-IR spectra measurements were followed as set forth in examples 1 and 2. CEG of 1-dodecyne shows a ν(C≡C) at 2176 cm$^{-1}$, 1-trimethylsilyldodecyne at 2176 cm$^{-1}$, and 1-dodecyne at 2120 cm$^{-1}$ (see FIG. 2).

EXAMPLE 5

Hydroboration of 1-Pentynyl

Figure 15:
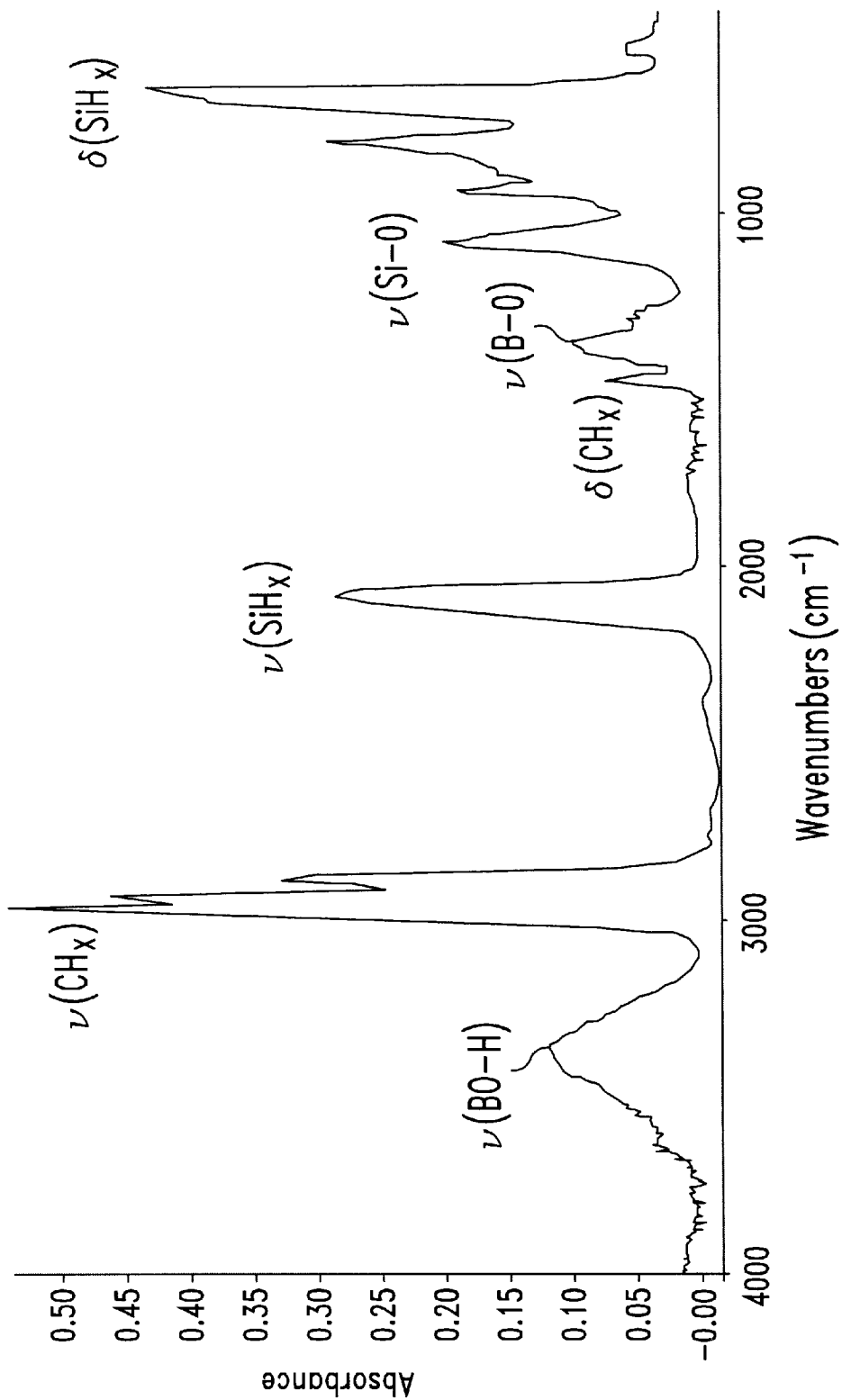
FIG. 15. BH3THF hydroborated 1-pentynyl.
Figure 16:
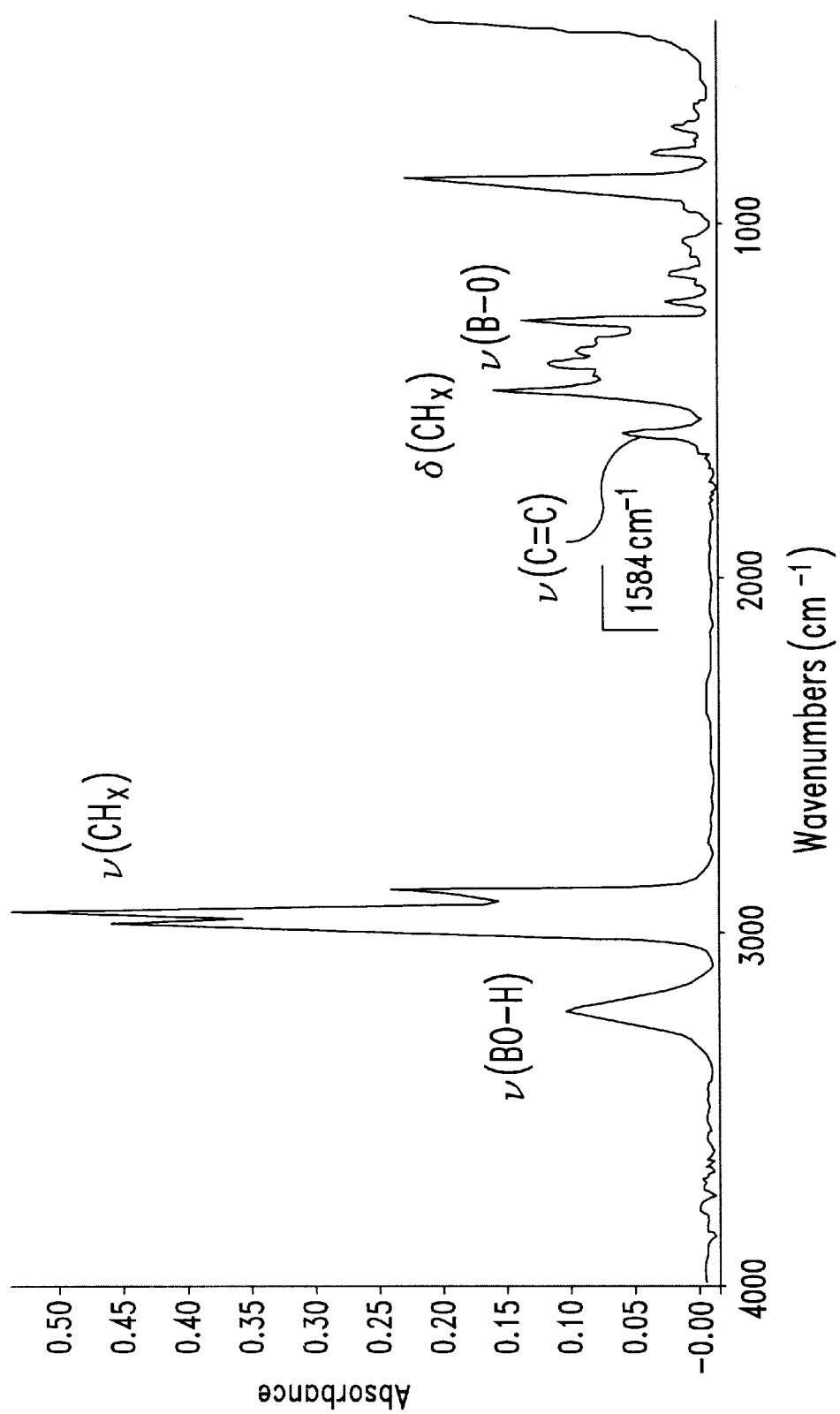
FIG. 16. Disiamylborane hydroborated 1-trimethylsilyl-dodecyne.
Figure 17:
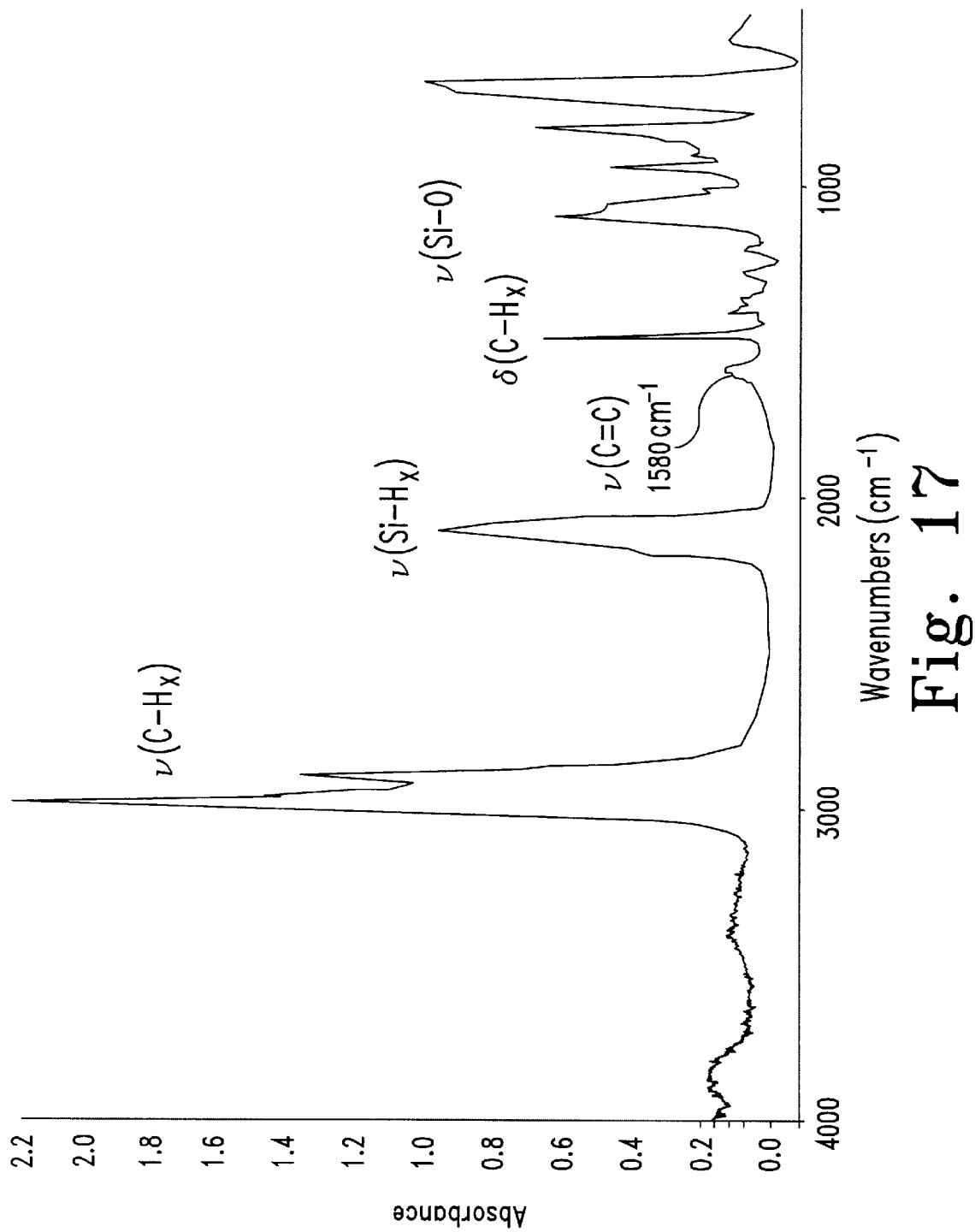
FIG. 17. Disiamylborane hydroborated 1-pentynyl.
Figure 18:
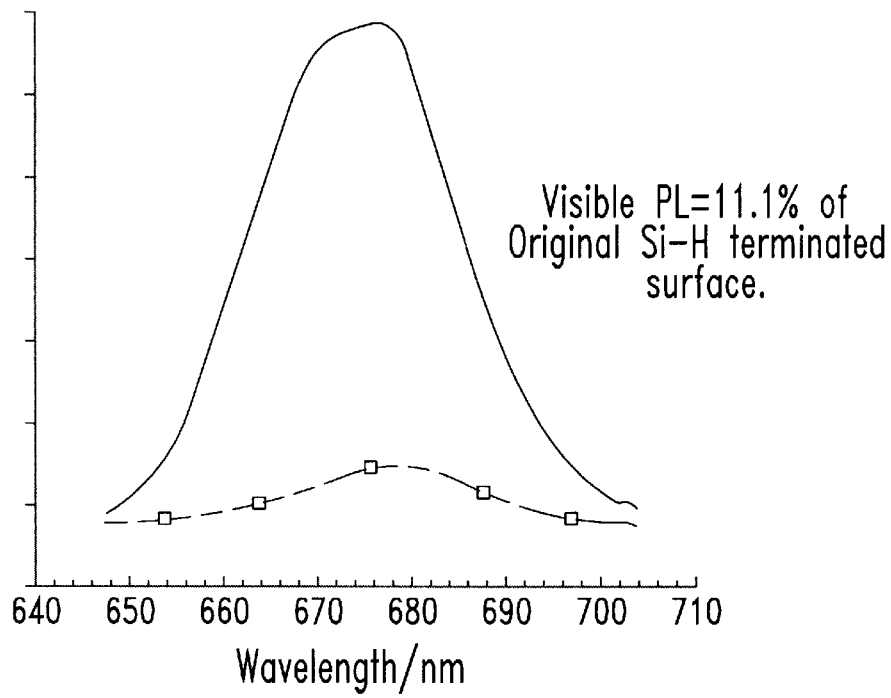
FIG. 18. Photoluminescence (PL) of freshly etched porous silicon (solid line) and 1-pentynyl (dotted line) grafted by CEG.
Figure 19:
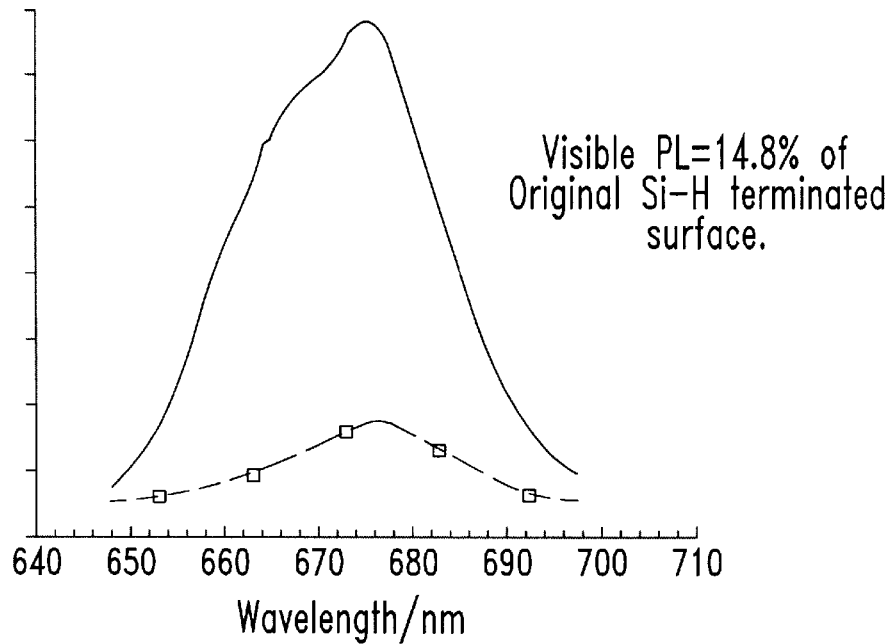
FIG. 19. PL of freshly etched porous silicon (solid line) and 1,7-octadiyne (dotted line) grafted by CEG.
Figure 20:
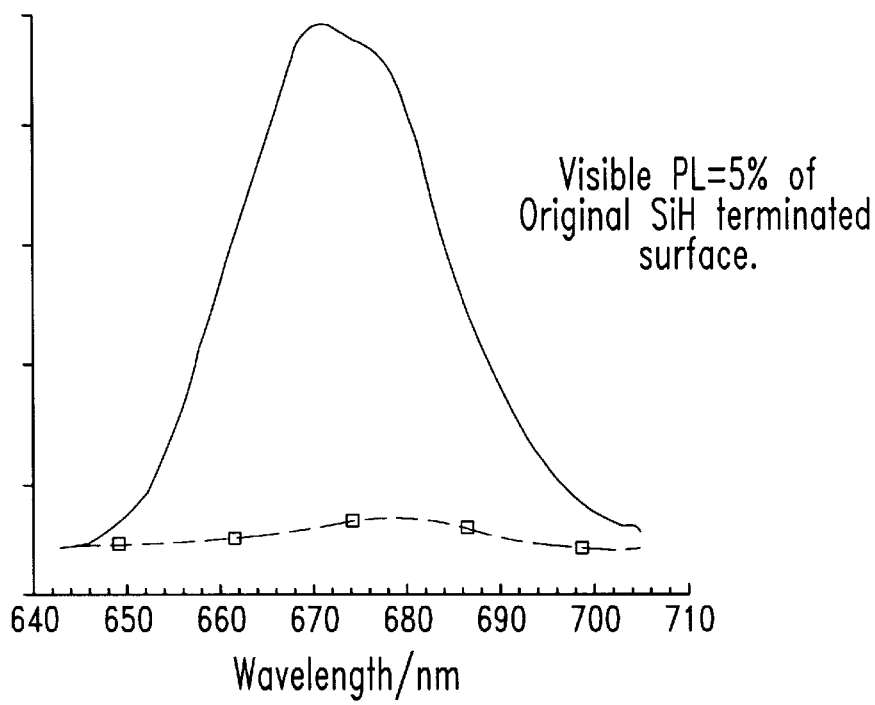
FIG. 20. PL of freshly etched porous silicon (solid line) and 1-dodecyne grafted by CEG (dotted line).

The same general procedures for preparation of porous silicon, electrografting, and FT-IR spectra measurements were followed as set forth in examples 1 and 2. The 1-pentyl surface was hydroborated with BH$_3$. THF or a 0.5 M THF solution of disiamylborane to verify the presence of the silylated triple bond (see FIGS. 15 and 17). The appearance of a broad band at 1580 cm$^{-1}$ and the concomitant consumption of the ν(C≡C) is indicative of a silylated, borylated double bond, which was verified by hydroboration of 1-trimethylsilyldodecyne and FT-IR analysis [ν(C≡C) at 1584 cm$^{-1}$)] (see FIG. 16).

EXAMPLE 6

FT-IR of AEG 1-Dodecyne

Figure 8:
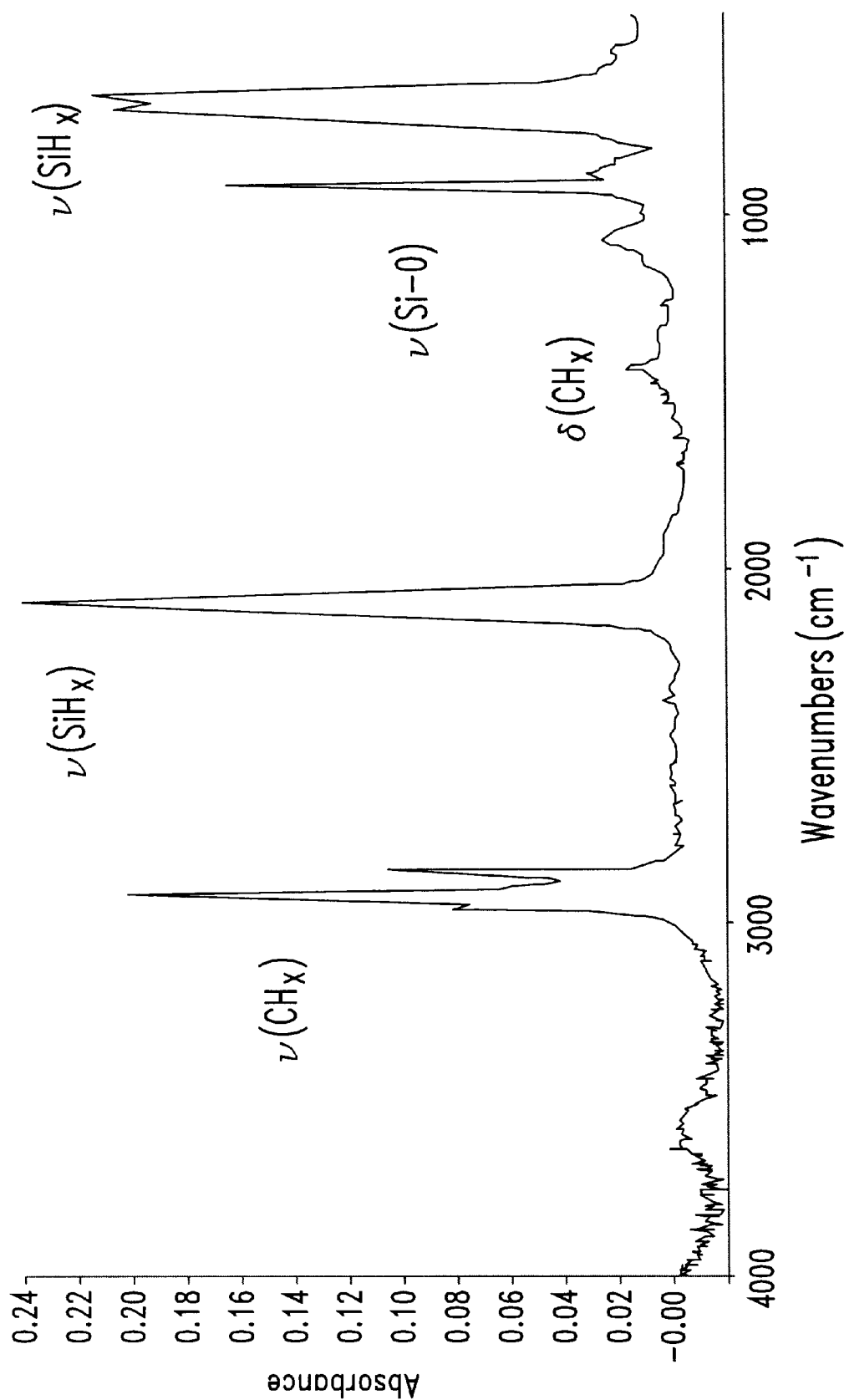
FIG. 8. AEG of 1-dodecyne.

The same general procedures for preparation of porous silicon, electrografting, and FT-IR spectra measurements were followed as set forth in examples 1 and 2. Covalent electrografting of alkynes also appears to occur when an anodic potential is applied, although AEG surfaces show complete reduction of all unsaturated bonds. The C≡C triple bond is not observed (~2180 cm$^{-1}$), along with only a weak vibration corresponding to a hydrosilylated double bond mode (1600 cm$^{-1}$) in the FT-IR spectra. In contrast to CEG, AEG of 1-dodecyne has features relating only to aliphatic C—H bonds (see FIG. 8).

EXAMPLE 7

FT-IR of AEG Phenylacetylene

Figure 9:
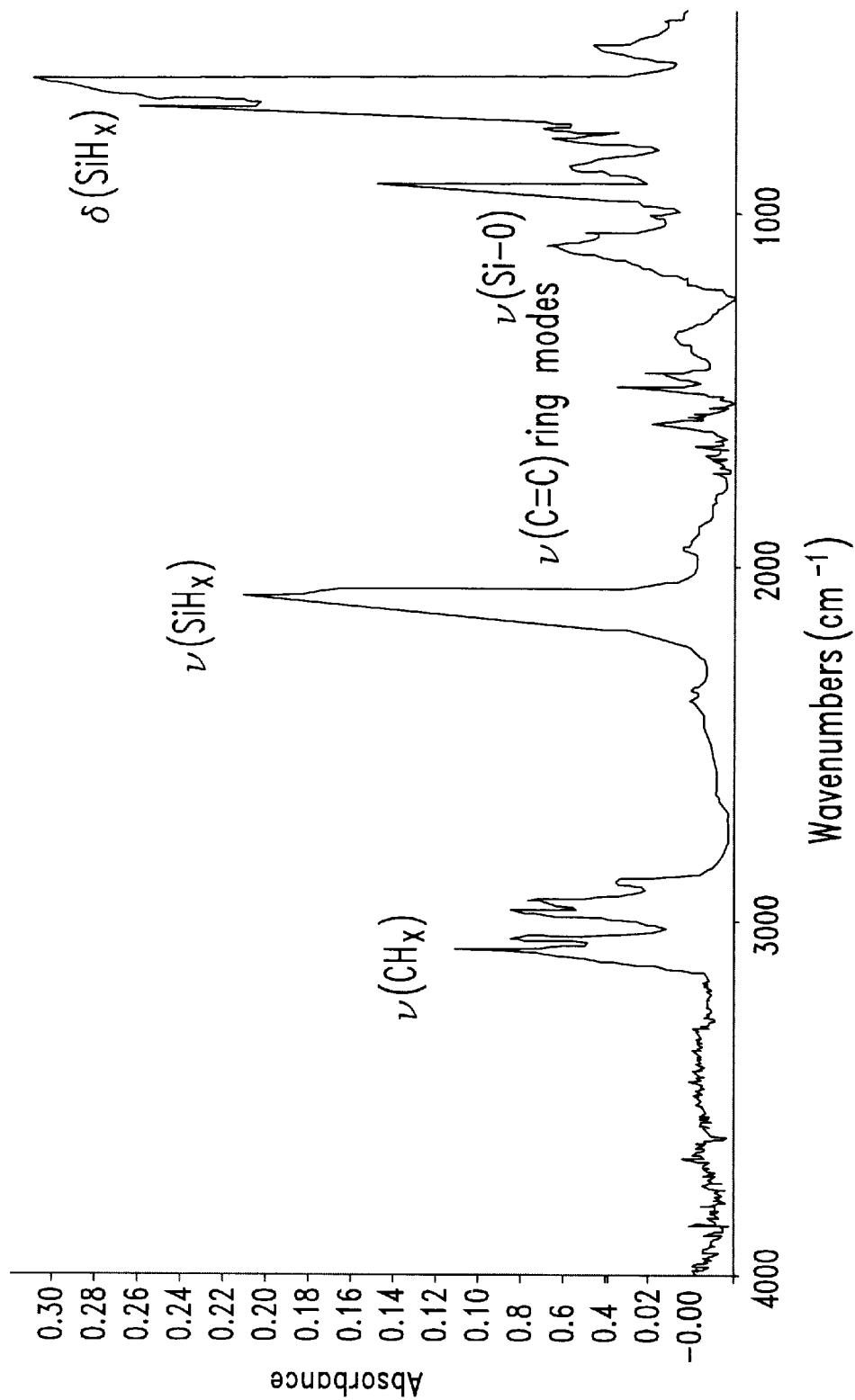
FIG. 9. AEG of phenylacetylene.

The same general procedures for preparation of porous silicon, electrografting, and FT-IR spectra measurements were followed as set forth in examples 1 and 2. In the spectrum of phenylacetylene AEG, ring breathing modes at 1599 cm$^{-1}$, 1493 cm$^{-1}$, and 1446 cm$^{-1}$ compare closely with polystyrene films and differ from those observed for the CEG surface of phenylacetylene at 1596 cm$^{-1}$, 1489 cm$^{-1}$, and 1443 cm$^{-1}$ (see FIGS. 4 and 9). Given the observations noted in FT-IR of the surfaces after AEG of 1-dodecyne and 1-phenylacetylene, it is likely that a surface-initiated cationic hydrosilylation mechanism is responsible for the Si—C bond formation in AEG reactions. Positive charges are stabilized in the depletion layer at the semiconductor-electrolyte interface, which are attacked by alkyne monomers. This can then be the starting point for a successive hydrosilylation or cationic polymerization reaction.

EXAMPLE 8

Boiling of Surfaces Functionalized Through AEG or CEG

Figure 10:
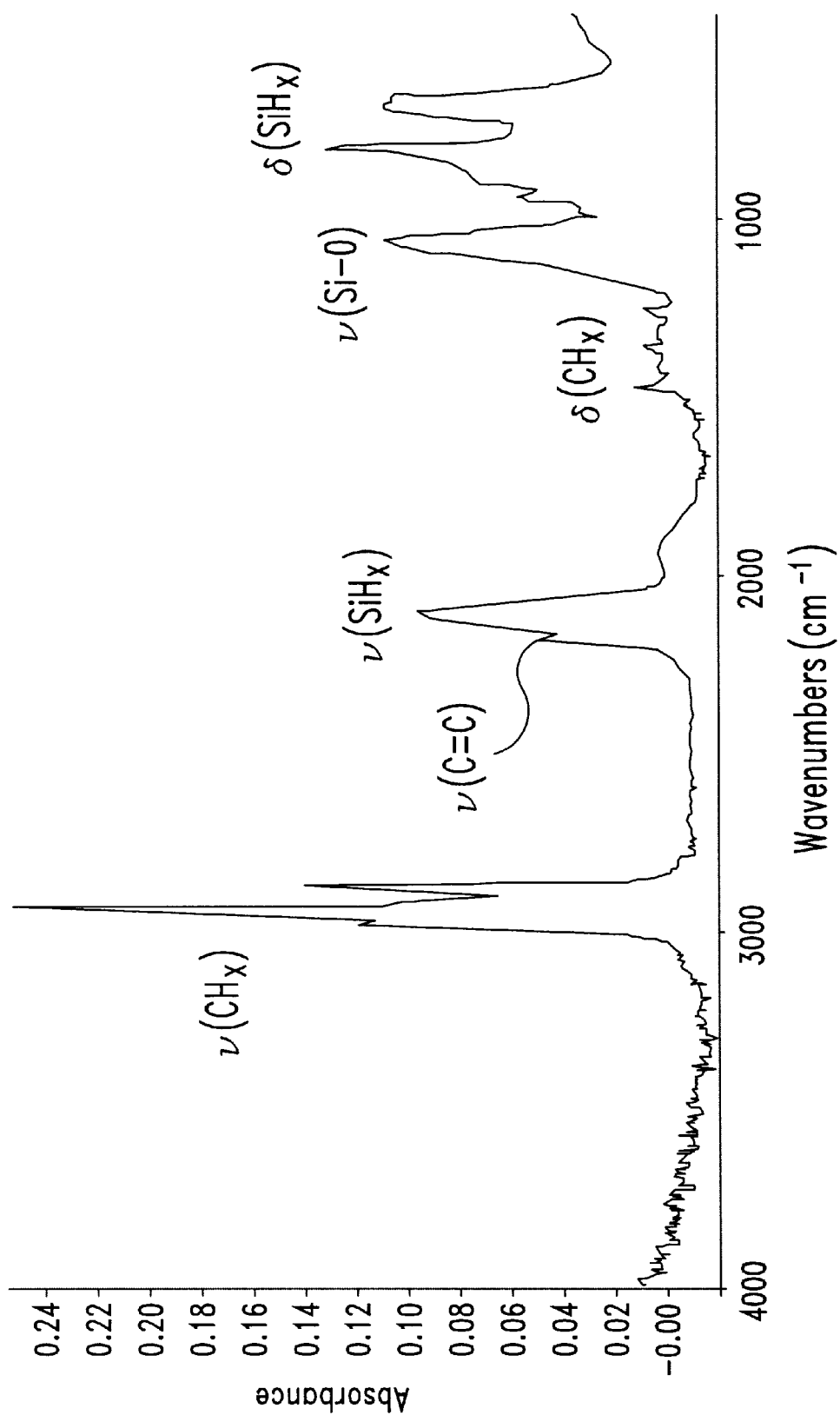
FIG. 10. CEG of 1-dodecyne after 10 minutes of boiling in NaOH.
Figure 11:
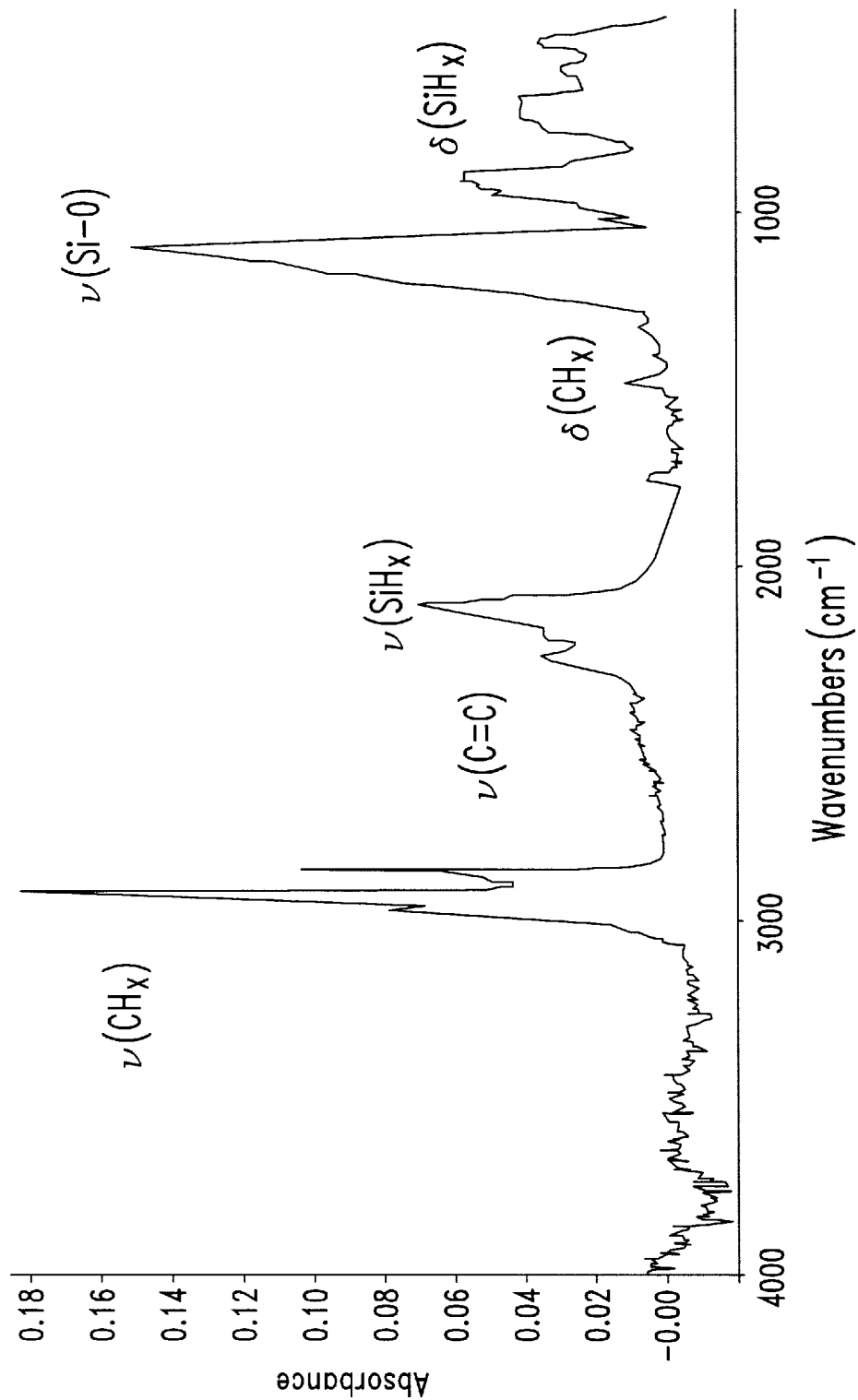
FIG. 11. AEG of 1-dodecyne after 10 minutes of boiling in NaOH.

The same general procedures for preparation of porous silicon, electrografting, and FT-IR spectra measurements were followed as set forth in examples 1 and 2. Boiling of the surfaces functionalized through AEG for 30 minutes in CHCl$_3$ results in no change in FT-IR, suggesting covalent bonding as opposed to physisorption. Based on the coincidence of the ring modes and the saturation of the C≡C bonds, we conclude that doubly hydrosilylated (bis-silylation) or possibly oligomeric material decorates the porous silicon surface (see FIG. 11). Stability tests using boiling aqueous NaOH solution (pH 10) demonstrate the chemical resistance of AEG and CEG samples compared to unfunctionalized porous silicon. Unmodified surfaces are destroyed when boiled in NaOH in about 180 seconds, while the CEG functionalized samples remain essentially unchanged after 10 minutes but for an increase in the v(Si—O) mode at 1050 cm$^{-1}$ (see FIG. 10). Extended treatment with ethanolic HF solution also results in no change in FT-IR spectra. The combined stability with respect to both HF and alkaline treatment is known only for Si systems with covalently attached organic layers.

EXAMPLE 9

Photoluminescence Spectra of CEG and AEG Samples

Figure 5:
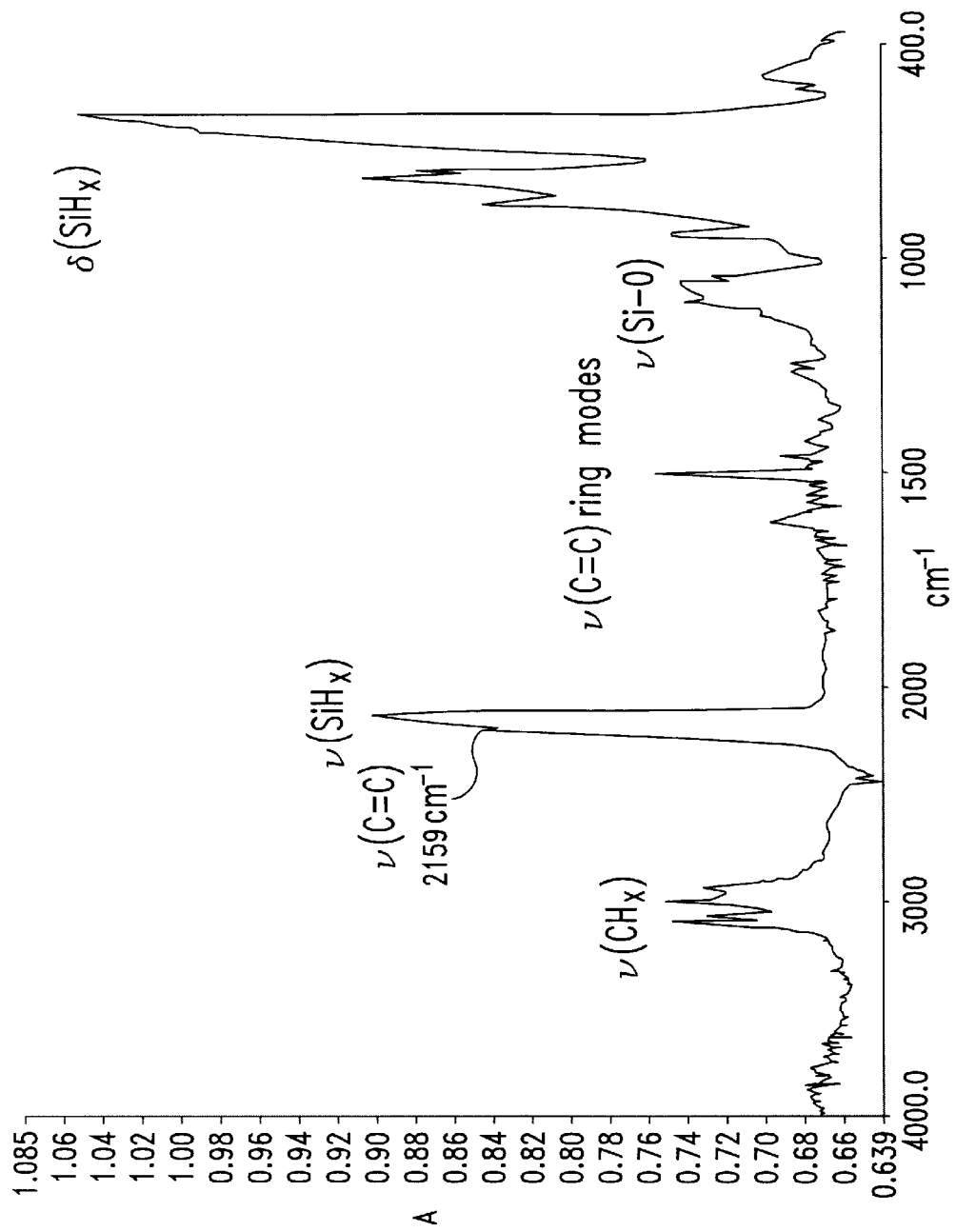
FIG. 5. CEG of p-Br-phenylacetylene.
Figure 6:
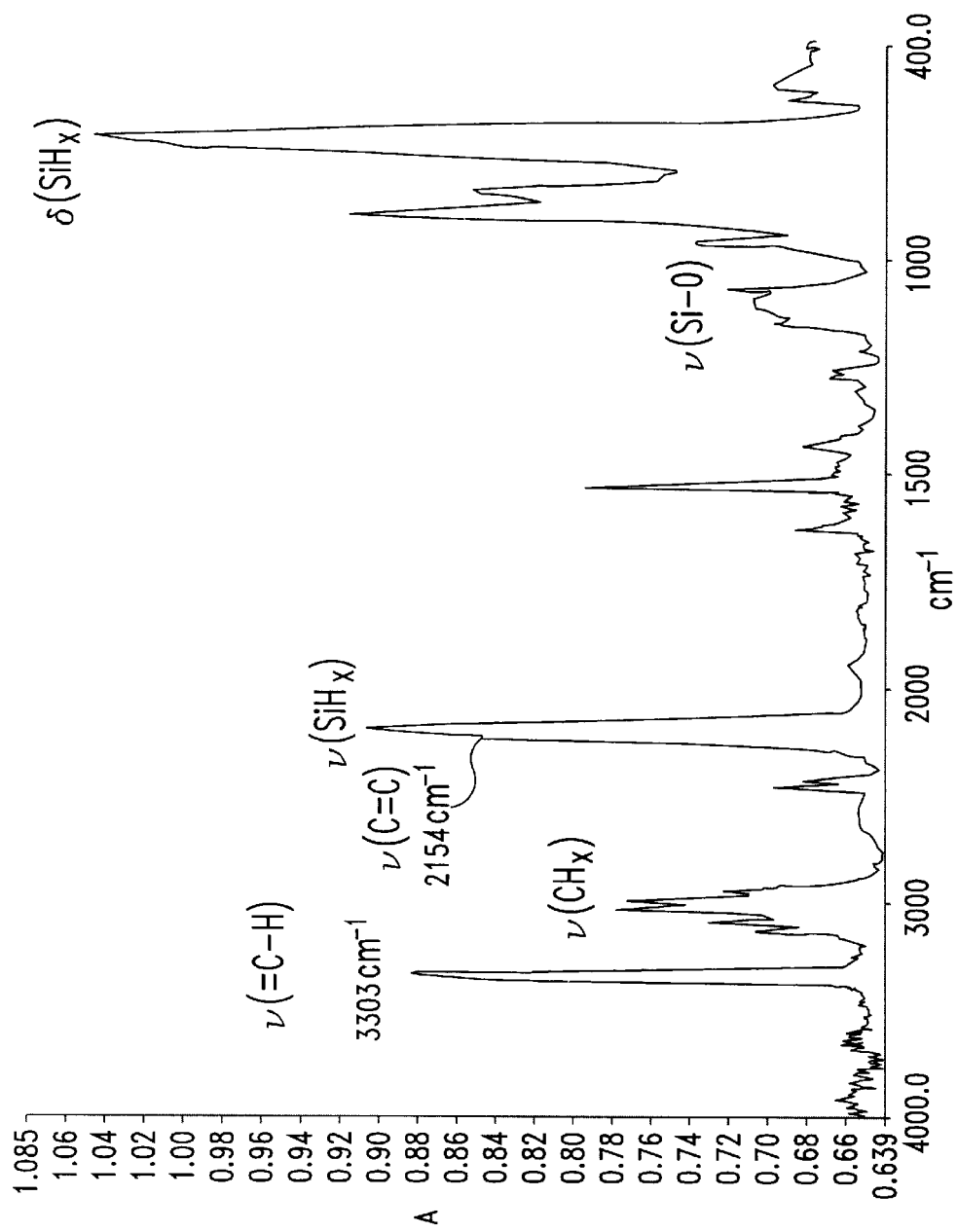
FIG. 6. CEG of 1,4-diethynylbenzene.
Figure 7:
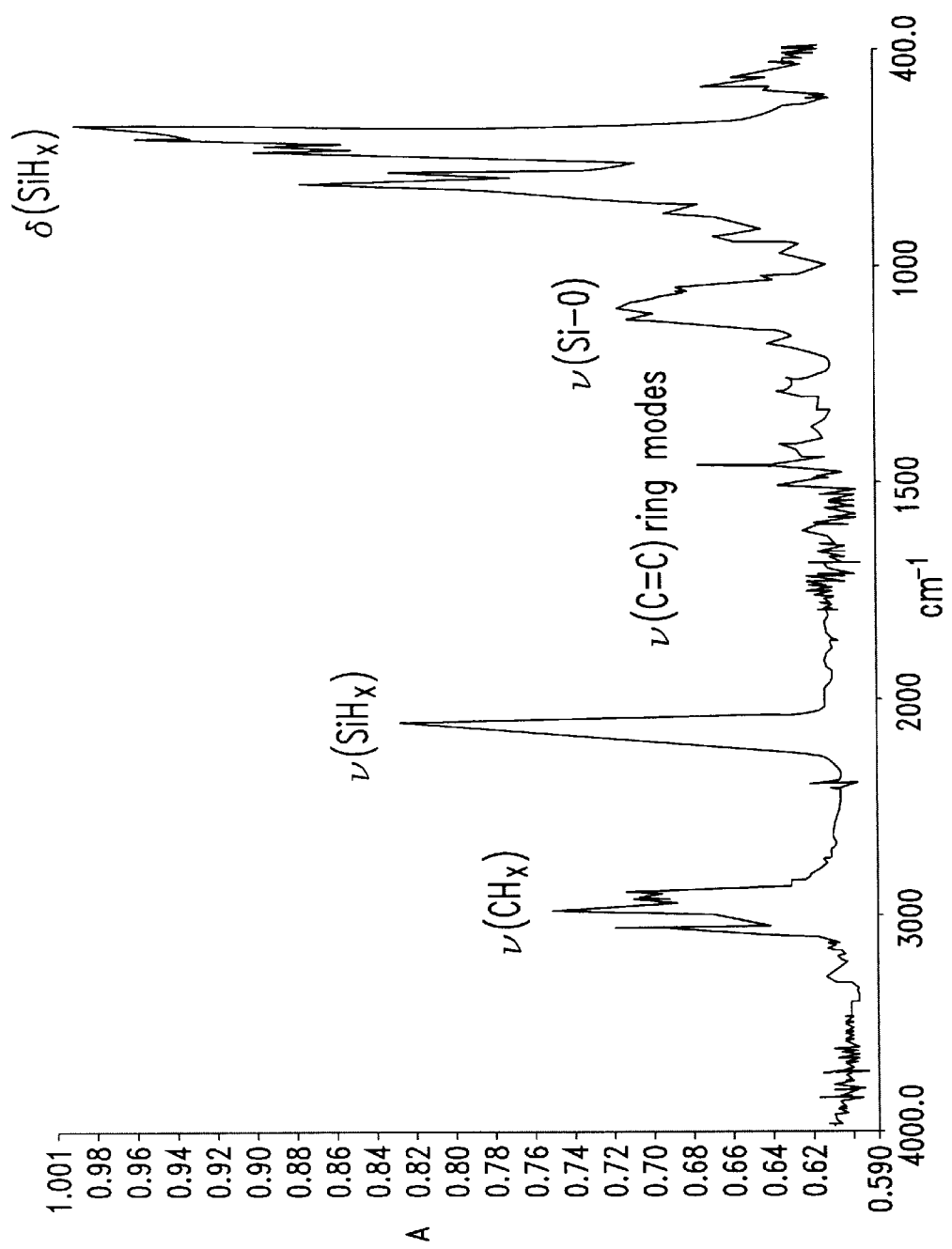
FIG. 7. CEG of diphenylphosphinnoacetylene.
Figure 13:
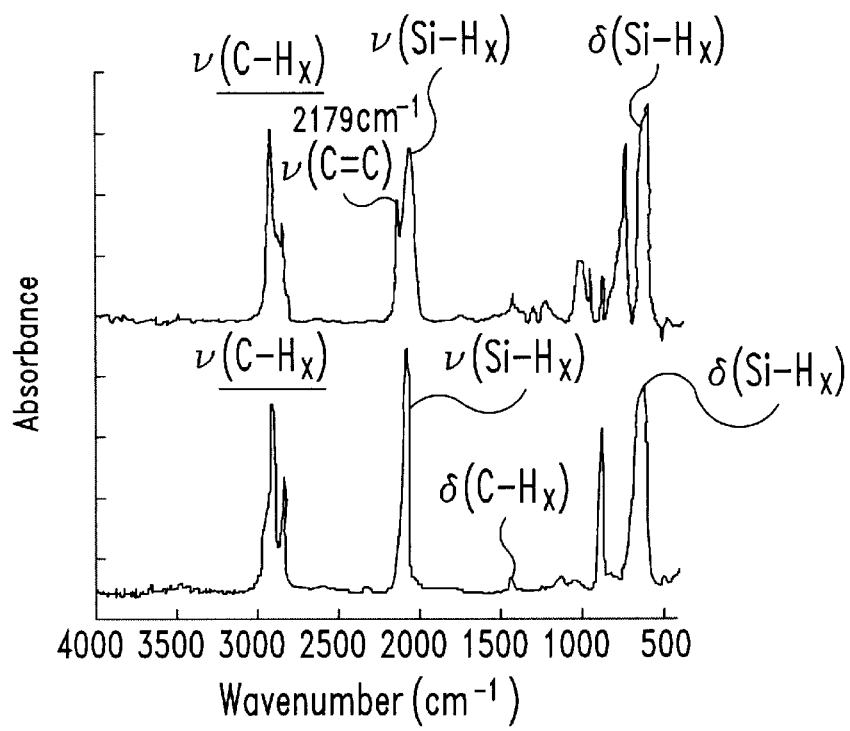
FIG. 13. CEG of 1-pentyne (top panel) and AEG of 1-dodecyne (bottom panel).
Figure 14:
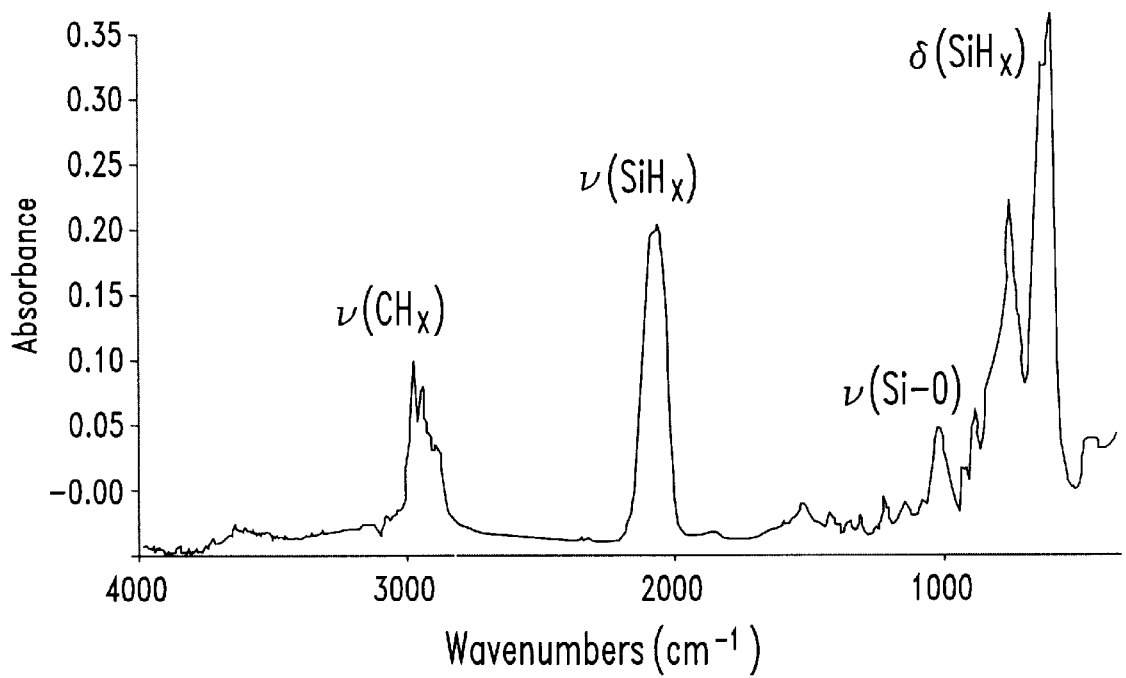
FIG. 14. CEG reaction carried out in the absence of alkyne.
Figure 21:
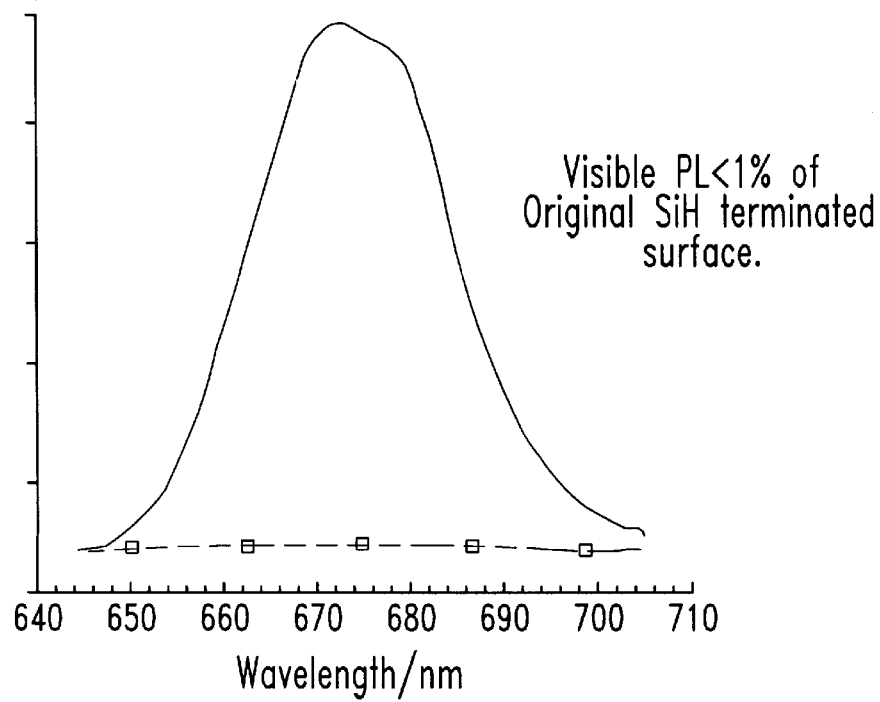
FIG. 21. PL of freshly etched porous silicon (solid line) and phenylacetylene (dotted line) grafted by CEG.
Figure 22:
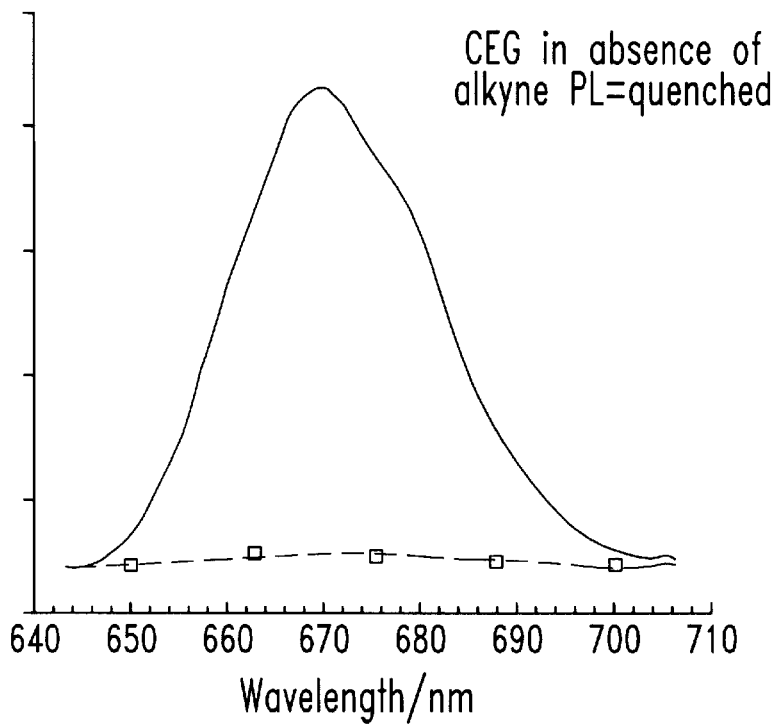
FIG. 22. PL of freshly etched porous silicon (solid line) and CEG in the absence of alkyne (dotted line).
Figure 23:
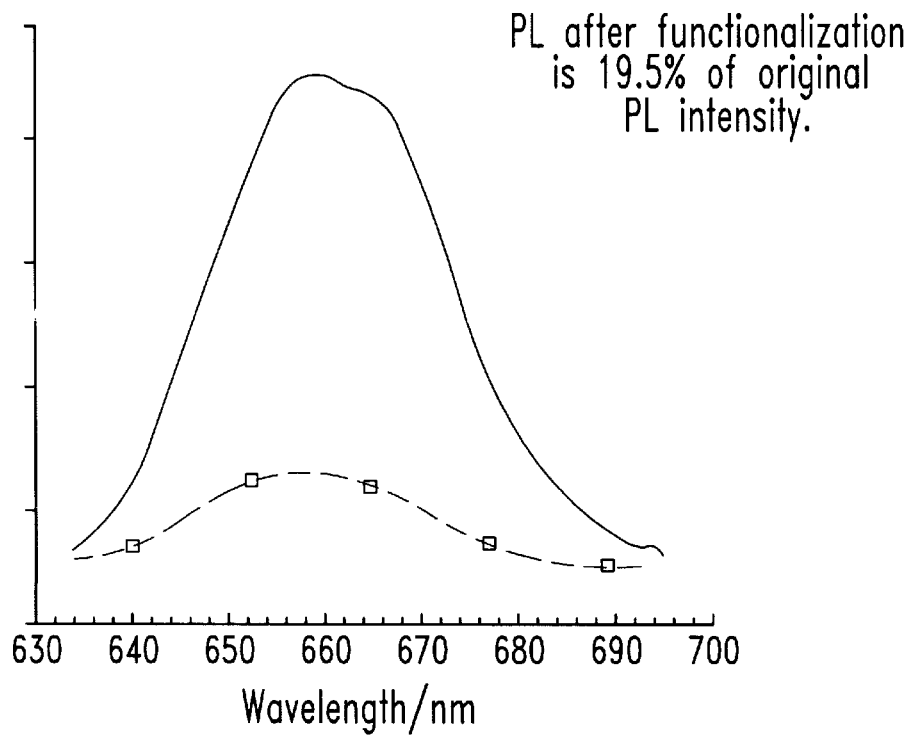
FIG. 23. PL of freshly etched porous silicon (solid line) and 1-dodecyne grafted by AEG (dotted line).

The same general procedures for preparation of porous silicon, electrografting, FT-IR spectra and photoluminescence measurements were followed as set forth in examples 1 and 2. Photoluminescence spectra of CEG samples show varying intensities depending on the surface type (see FIGS. 1 and 13). Upon CEG of 1-dodecyne, 1,7-octadiyne, and 1-pentynyl (see FIGS. 2–3 and 18–20) the surfaces retain between about 5 to 15% of the light emission, with a small red-shift of ~10 nm relative to freshly prepared porous silicon ($\lambda_{max}$=663 nm). The phenethynyl surface (arynyl group) and other highly conjugated alkynyl terminated surfaces (see FIGS. 5–7) show no light emission whatsoever as previously reported. AEG samples have more intense PL, with ~20% remaining for the alkyl protected surface as compared to the etched hydride terminated surface (see FIG. 21).

What is claimed is:

1. A method for forming a covalently bound monolayer of organic substituents on a silicon substrate having a surface comprising silicon hydride groups, said method comprising the steps of:

contacting the surface of the silicon substrate with an electrically conductive, substantially oxygen-free, aprotic organic solvent solution comprising an optionally substituted C$_2$–C$_{24}$ alkyne;

positioning a conductor electrode in electrical current flow communication with said solution; and applying an electrical potential to said solution between the silicon surface and the conductor electrode sufficient to induce electrical current flow through said solution between the silicon surface and the conductor electrode for a period of time sufficient to covalently bind at least a portion of the alkyne to the silicon surface.

2. The method of claim 1 wherein the electrical potential is applied so that the silicon substrate serves as an anode.

3. The method of claim 1 wherein the electrical potential is applied so that the silicon substrate serves as a cathode.

4. The method of claim 1 wherein the alkyne is a compound of the formula:

wherein

R$^1$ is hydrogen and R$^2$ is hydrogen, hydroxy, halo, cyano, isocyano, C$_1$–C$_{18}$ alkoxy, C$_1$–C$_{18}$ carboxy, C$_1$–C$_{18}$ alkoxycarbonyl, primary, secondary or tertiary amino, thiol, optionally substituted phosphino, borane (1) or borane (2), or C$_1$–C$_{18}$ alkylthioether or an optionally substituted C$_1$–C$_{18}$ alkyl, aryl, heteroaryl or vinyl group; and when R$^2$ is a substituted group, the group is substituted with one or more substituents selected from the group consisting of hydroxy, halo, cyano, isocyano, C$_2$–C$_{24}$ alkynyl, C$_1$–C$_{18}$ alkoxy, C$_1$–C$_{18}$ carboxy, C$_1$–C$_{18}$ alkoxycarbonyl, primary, secondary or tertiary amino, thiol, optionally substituted phosphino, aryl, borane (1) or borane (2), or C$_1$–C$_{18}$ alkylthioether, halo C$_1$–C$_{18}$ alkyl, cyano C$_1$–C$_{18}$ alkyl, isocyano-C$_1$–C$_{18}$ alkyl, C$_1$–C$_{18}$ carbamido, or C$_1$–C$_{18}$ alkylthio group, a C$_1$–C$_{18}$ ferrocene substituent or another electron donor, a metal chelating ligand or a metal complex thereof, or a biologically significant ligand selected from an antibody, a receptor protein, DNA or RNA, or a DNA or RNA analog capable of forming a double or triple stranded complex with DNA or RNA.

5. The method of claim 4 wherein the silicon substrate serves as an anode.

6. The method of claim 4 wherein the silicon substrate serves as a cathode.

7. The method of claim 4 wherein R$^2$ substituent is a substituted group wherein the substituent is an optionally protected hydroxy, carboxy, amino or thiol, said method further comprising the step of covalently coupling a biologically significant ligand to the silicon substrate through the substituent group.

8. The method of claim 4 wherein the silicon substrate is a porous silicon substrate.

9. The method of claim 4 wherein the silicon substrate is a flat silicon substrate.

* * * * *